US009285276B2

(12) United States Patent
Fraden (10) Patent No.: US 9,285,276 B2
(45) Date of Patent: Mar. 15, 2016

(54) PROBE COVER WITH MATCHING FEATURE FOR A MEDICAL THERMOMETER

(71) Applicant: Kaz USA, Inc., Southborough, MA (US)

(72) Inventor: Jacob Fraden, San Diego, CA (US)

(73) Assignee: Helen of Troy Limited, St. Michael (BB)

( * ) Notice: Subject to any disclaimer, the term of this patent is extended or adjusted under 35 U.S.C. 154(b) by 0 days.

(21) Appl. No.: 13/747,918

(22) Filed: Jan. 23, 2013

(65) Prior Publication Data

US 2013/0128926 A1    May 23, 2013

Related U.S. Application Data (62) Division of application No. 12/675,877, filed as application No. PCT/US2009/069528 on Dec. 24, 2009, now Pat. No. 8,882,347.

(60) Provisional application No. 61/203,641, filed on Dec. 29, 2008.

(51) Int. Cl.
*G01K 1/08* (2006.01)
*G01J 5/02* (2006.01)

(52) U.S. Cl.
CPC ... *G01K 1/08* (2013.01); *G01J 5/02* (2013.01); *G01J 5/021* (2013.01)

(58) Field of Classification Search
USPC .................................................. 374/209, 158
See application file for complete search history.

(56) References Cited

U.S. PATENT DOCUMENTS

| 4,159,766 A | 7/1979 | Kluge |
| 4,662,360 A | 5/1987 | O'Hara et al. |
| 5,088,834 A | 2/1992 | Howe et al. |
| 5,163,418 A | 11/1992 | Fraden et al. |

(Continued)

FOREIGN PATENT DOCUMENTS

| CN | 1720429 A | 11/2006 |
| TW | 410272 B | 11/2000 |
| WO | WO 2008117670 A1 * | 10/2008 |

OTHER PUBLICATIONS

Translation of WO 2008/117670 (Feb. 10, 2008).*

(Continued)

*Primary Examiner* — Mirellys Jagan
(74) *Attorney, Agent, or Firm* — Stroock & Stroock & Lavan LLP (57) ABSTRACT

A probe cover for medical thermometer has a matching feature for preventing its use with an incompatible thermometer. A mechanical matching feature of the probe cover includes at least one of a fold, a step, or a series of holes or indentations that are respectively matched to a ridge, a valley or series of pins formed on the front end of a compatible thermometer. When applied to the compatible thermometer, the mechanical matching feature permits the probe cover to be fully seated on and retained by the probe, thereby placing the thermometer in condition for use. Alternatively, an opto-electronic matching feature of the probe cover includes a reflective layer for use with an opto-electronic detection circuit of a compatible thermometer. When applied to the compatible thermometer, the opto-electronic detection detects the reflective layer and places the compatible thermometer in an operational state for use.

4 Claims, 9 Drawing Sheets (56) References Cited

U.S. PATENT DOCUMENTS

| | | |
|---|---|---|
| 5,179,936 A | 1/1993 | O'Hara et al. |
| 5,293,862 A | 3/1994 | O'Hara et al. |
| 5,411,032 A | 5/1995 | Esseff et al. |
| 6,022,140 A | 2/2000 | Fraden |
| 6,139,182 A | 10/2000 | Levatter et al. |
| 6,309,671 B1 | 10/2001 | Foster et al. |
| 6,461,037 B1 | 10/2002 | O'Leary |
| 6,513,970 B1 | 2/2003 | Tabata et al. |
| 6,619,837 B2 | 9/2003 | Walls et al. |
| 6,647,284 B1 | 11/2003 | Lee |
| 6,789,936 B1 | 9/2004 | Kraus et al. |
| 6,850,789 B2 | 2/2005 | Schweitzer, Jr. et al. |
| 7,354,194 B2 | 4/2008 | Walker et al. |
| 7,520,671 B2 | 4/2009 | Lantz et al. |
| 7,572,056 B2 | 8/2009 | Lane et al. |
| 7,815,367 B2 | 10/2010 | Lane et al. |
| 8,136,986 B2 | 3/2012 | Lane et al. |
| 2002/0186746 A1* | 12/2002 | Tomioka et al. ............... 374/121 |
| 2006/0165152 A1* | 7/2006 | Walker et al. .................. 374/158 |
| 2007/0147474 A1* | 6/2007 | Lantz et al. .................... 374/208 |
| 2007/0189358 A1 | 8/2007 | Lane et al. |
| 2009/0129437 A1 | 5/2009 | Chuang et al. |
| 2011/0014112 A1* | 1/2011 | Misra ............................. 423/446 |
| 2011/0257521 A1* | 10/2011 | Fraden .......................... 600/438 |
| 2012/0076169 A1 | 3/2012 | Hsieh |

OTHER PUBLICATIONS

International Search Report and Written Opinion dated Feb. 25, 2010 issued in PCT/US2009/069528.

International Preliminary Report on Patentability dated Jul. 7, 2011 issued in PCT/US2009/069528.

Office Action dated Nov. 19, 2012 issued in CN200980153128.9.

* cited by examiner

PROBE COVER WITH MATCHING FEATURE FOR A MEDICAL THERMOMETER

CROSS-REFERENCE TO RELATED APPLICATION

The present application is a divisional application of U.S. patent application Ser. No. 12/675,877, filed on Dec. 29, 2012, which was the National Stage of International Application No. PCT/US09/69528, filed on Dec. 24, 2009, which claims priority under 35 U.S.C. §119(e) to U.S. Provisional Application No. 61/203,641, filed on Dec. 29, 2008 and entitled "Matching Probe Cover for Infrared Thermometer," the contents of all of which are hereby fully incorporated by reference herein.

FIELD OF THE INVENTION

The present invention relates generally to thermometers, and more particularly, to medical thermometers that employ disposable or reusable probe covers.

BACKGROUND OF THE INVENTION

The temperature of a human or animal, can be measured either by means of thermal conduction or thermal radiation. In the former case, a temperature sensing probe may be positioned inside the patient's body cavity or on the skin surface to obtain an intimate contact for conductively receiving thermal energy indicative of a surface temperature of a patient-measured body site. In the latter case, a naturally-emanated electromagnetic radiation in the mid- and far-infrared spectral ranges may be detected by an appropriate non-contact sensor, whose output signal is indicative of the surface temperature of a patient-measured body site (for example, in proximity to the tympanic membrane). A combination of a sensor, electronic circuit and other components form an infrared (IR) thermometer, which is an opto-electronic instrument.

Many medical thermometers, either contact or non-contact, use sanitary probe covers which envelope the probe and prevent cross-contamination of patients and soiling of the probe. In a contact probe cover, thermal energy (heat) is transmitted by means of thermal conduction. Thus, requirements for the probe cover must be compatible with the thermally conductive properties of the probe cover material. Various conventional covers for such contact thermometers are described in many patents, for example, in U.S. Pat. No. 4,159,766 to Kluge, which is incorporated by reference herein in its entirety.

In order to measure a surface temperature of an object by means of IR radiation, the probe of the IR thermometer is aimed at the area of interest. For example, in order to measure the temperature of a tympanic membrane and the surrounding tissues, the probe is placed into the ear canal. Before the insertion, a probe cover is typically installed onto the probe to envelope its parts that otherwise might come in contact with the tissues of the ear canal.

Figure 1A:
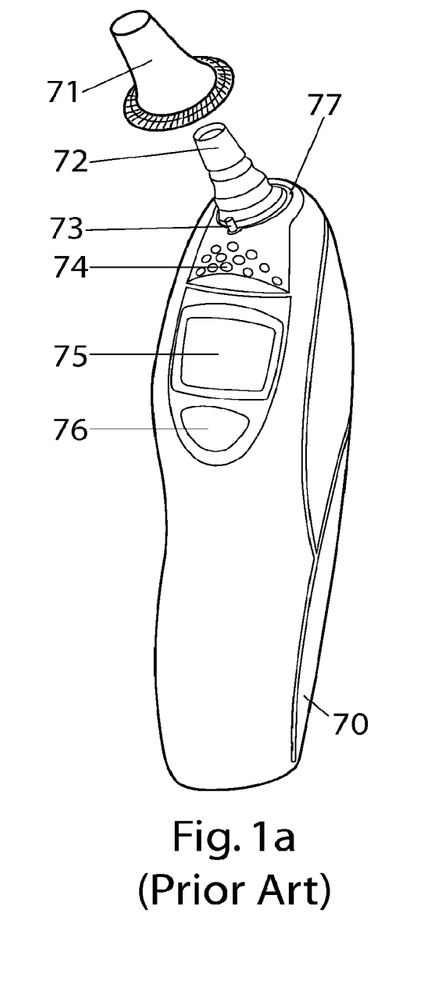
FIGS. 1a and 1b show a front perspective view and a rear perspective view of a prior art infrared thermometer, respectively.
Figure 1B:
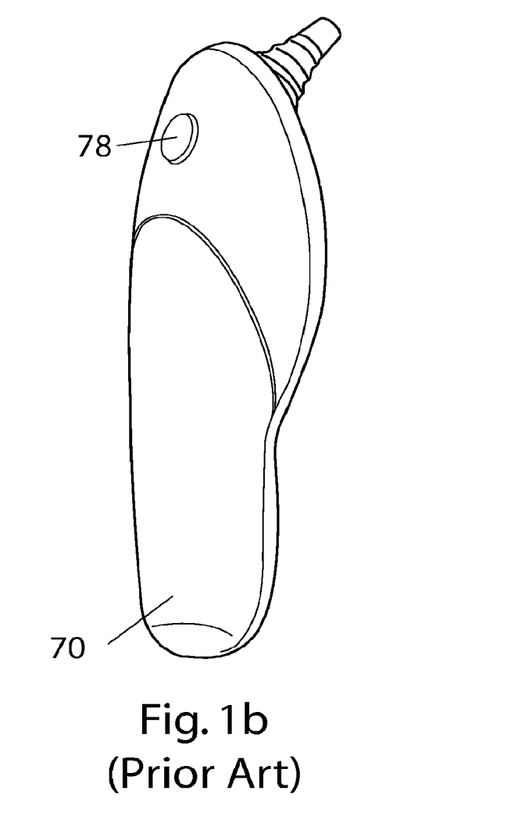

A typical prior art infrared thermometer 70 is illustrated in FIGS. 1a and 1b. The thermometer 70 includes a front end 77, from which an infrared probe 72 projects, for example, with an orientation suitable for placement of the probe 72 in the ear canal. A probe cover 71 is positioned to be placed over the probe 72 for eliminating any direct contact between the probe 72 and tissues of the ear canal. A power button 76 is provided for powering the circuitry of the thermometer 70. A start button 78 is provided to engage the circuitry to perform a temperature measurement, and a display 75 is provided, for example, to indicate a current condition or status of the thermometer 70 and/or the results of a current temperature measurement. A probe cover detector 73 is positioned near a base of the probe 72 for detecting that the probe cover 71 has been placed over the probe 72, and may for example interact with the circuitry to permit operation of the thermometer 70 only when installation of the probe cover 71 has been detected. After a temperature measurement has been made, a probe cover ejector 74 elevates the front end 77 of the thermometer 70 relative to the probe 72 in order to eject the probe cover 71 from the probe 72.

The probe cover 71 is not only required to provide a sanitary protection against contamination of the probe by earwax and other soiling biological compounds, but it must possess other properties for accurate temperature measurement by means of detecting an associated IR signal. Such properties, for example, include a good optical transparency of the probe cover in the spectral range of interest, low directional distortion of optical rays, tight manufacturing tolerances, stability of the optical properties during installation onto the probe, long term stability, and the like. Suitable probe covers for IR thermometers are exemplified by U.S. Pat. No. 5,088,834 issued to Howe et al. and U.S. Pat. No. 5,163,418 issued to Fraden et al., each of which is incorporated by reference herein in its entirety. Most prior art probe covers are formed to surround a longitudinal axis of a thermometer probe.

Figure 2A:
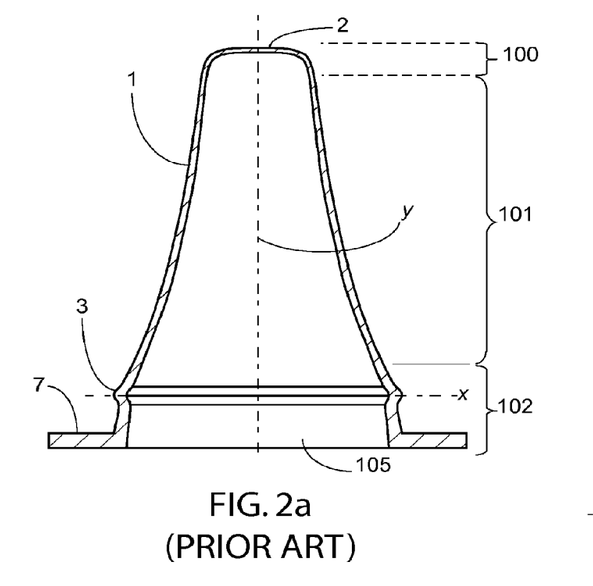
FIGS. 2a and 2b shows a unitary prior art probe cover and a two-piece prior art cover, respectively.

As a rule, a prior art probe cover intended for a medical thermometer includes three portions being disposed along the probe longitudinal axis y (see, e.g., FIG. 2a):

1) a proximal or "base" portion 102 provided for physical retention of the cover by the thermometer probe or front end of a thermometer housing. The proximal portion 102 may contain an offset 3 for interaction with the retention devices of the probe. This offset 3 is disposed along a transverse axis x that is substantially normal to longitudinal axis y. A brim 7 may or may not be part of the proximal portion 102. The proximal portion 102 has an opening 105 through which the probe is inserted during a probe cover installation. Instead of or in addition to the offset 3, the proximal portion 102 may have a snug fit over the probe, thus using friction as a retention force (see, e.g., FIG. 2e), 2) a middle or "body" portion 101 provided for enveloping the sides of the probe. The middle portion 101 includes a rigid or pliant wall 1. The middle portion 101 may be prefabricated, or it may be formed during the probe cover installation by stretching wall 1 to match the probe length, and 3) a distal or "tip" portion 100 provided for enveloping the optical end of the probe of an IR thermometer or the sensing part of a contact thermometer. This portion 100 contains a membrane 2 which is substantially transparent for IR radiation (for an IR thermometer), or is thermally conductive (for a contact thermometer). The membrane 2 may include a polymer film (for an IR thermometer, in thickness ranges from as little as 0.0005 in. to as much as 0.005 in.). The IR radiation passes through the membrane 2 before entering the probe where it is detected by the IR sensor. In effect, the membrane 2 of the probe cover works as an optical filter, and often is alternatively called a "lens filter."

Figure 2B:
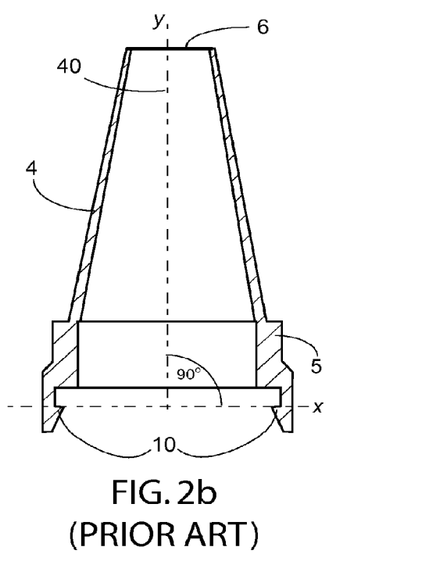

Typical materials for fabricating the probe covers are polyethylene, polypropylene, and copolymers of polyethylene and polypropylene. FIG. 2a shows a prior art unitary probe cover (as taught for example by U.S. Pat. No. 5,088,834) which is fabricated as a single piece. FIG. 2b shows a two-piece probe cover (as taught by U.S. Pat. Nos. 4,662,360, 5,293,862 and 5,179,936, each issued to O'Hara et al. and incorporated by reference herein in their entirety) where a membrane 6 is welded onto a frustoconical body 4. In the probe cover of FIG. 2b, a bottom ring 5 is provided for affixing the probe cover to the probe as part of a proximal portion. Probe covers generally have shapes that follow a body of rotation around a longitudinal axis y.

Figure 2C:
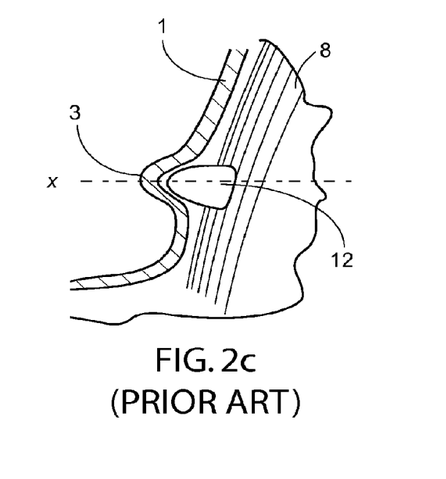
FIGS. 2c and 2d show partial views of prior art probe covers having offset and hook retention mechanisms, respectively.

Probe covers may be attached to the probe or the IR thermometer housing by various mechanisms. FIG. 2c once again shows the offset 3, which is an extension of wall 1 of the probe cover in the proximal portion 102. The offset 3 engages a nipple 12 that is part of a probe 8 of the IR thermometer when the probe cover is installed onto the probe 8. The nipple 12 is disposed along a transverse axis x.

Figure 2D:
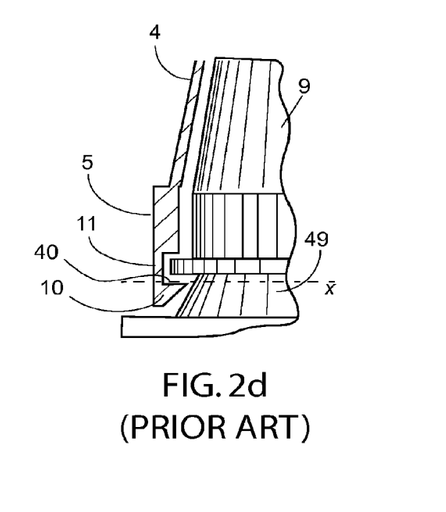
Figure 2E:
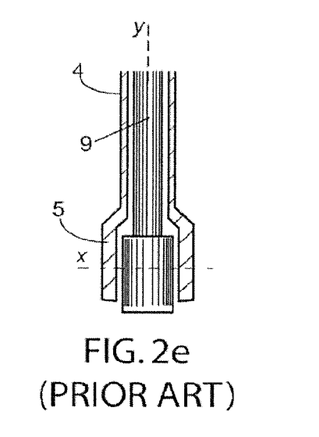
FIG. 2e shows a prior art probe cover including a friction ring for retention.

Another known way of attaching a probe cover to a probe is shown in FIG. 2d. FIG. 2d illustrates a hook 10 (also illustrated in FIG. 2b) which is supported by a neck 11. The neck 11 is an extension of a ring 5. When the probe cover is installed onto the probe 9, hook 10 engages a retention skirt 49 of a probe cover 9. The retention portion 40 of hook 10 is disposed along the transverse axis x. Alternatively, FIG. 2e shows a probe cover 4 installed on a probe 9, which includes a retention ring 5 that enables the probe cover 4 to be retained by a frictional force applied to the probe cover 4 along the transverse axis x.

In the prior art probe covers illustrated in FIGS. 2a-2e, a probe cover body is formed along the longitudinal axis y, having retention elements formed along the transverse axis x.

Known prior probe covers, while having various shapes and methods of retention, often may be interchanged between different types of thermometers. This is undesirable, and may for example cause a mismatch between the type of a membrane 2 (material, thickness and shape) and the thermometer calibration and, as a result, cause unacceptably high errors in temperature measurement. It is important to use only a correct (matching) probe cover with a particular thermometer. However, common matching techniques such as affixing an identification code on a probe cover are typically insufficient for preventing use of a wrong probe cover. Thus, a more direct method for preventing usage of a foreign probe cover on a thermometer is desirable.

SUMMARY OF THE INVENTION

The present invention is directed to a probe cover that encourages proper use with a thermometer probe by forming matching elements on a proximal portion of the probe cover to be matched with corresponding elements on a front end of the thermometer in proximity to the probe. The matching elements have complementary features to the corresponding elements on the thermometer probe (for example, complementary or interlocking shapes) that form a "key-lock" pair when the probe cover is installed onto the probe. A mismatching of non-corresponding elements makes it impossible either to securely position the probe cover on the probe and/or operate the thermometer. The method of matching can be used for any type of a medical thermometer having a probe cover (including, for example, IR and contact thermometers).

BRIEF DESCRIPTION OF THE DRAWINGS

The foregoing and other features of the present invention will be more readily apparent from the following detailed description and drawings of illustrative embodiments of the invention in which:

FIG. 11b shows a cross-sectional view through a portion of a brim of the probe cover of FIG. 11a;

FIG. 12 shows a side view of a probe cover according to another embodiment of the present invention;

Like reference numerals are used in the drawing figures to connote like components of the probe cover.

DETAILED DESCRIPTION OF THE PREFERRED EMBODIMENTS

A probe cover for an infrared (IR) thermometer is a sanitary envelope which forms a barrier between the instrument and the patient. For the purpose of illustrating principles of the present invention, several probe covers are described and shown for application to an infrared thermometer used in measuring temperatures in an ear canal of a human or animal. The present invention is however equally applicable to probe covers used in a variety of other contexts, for example, including medical contact thermometers that take conductive temperature measurements from a body cavity or surface of a human and veterinary thermometers used for determining the temperature of an animal.

In the presently-described examples, a distal portion of the probe cover is designed to cover a window of a probe housing through which IR energy is received in order to measure temperature. The material for the probe cover's distal portion (that is, for its "optical portion") is preferably selected from the group of polymers which have significant transparency in the spectral range between 3 and 15 µm. Examples of suitable polymers include polyethylene, polypropylene, and copolymers of polyethylene and polypropylene. As a rule, the thickness of the optical portion of the cover is preferably on the order of 20 micrometers. This thickness provides acceptable IR transmission characteristics, as well as an acceptable mechanical strength. As shown for example in FIG. 3, a body 1, 2 of the probe cover is substantially symmetrical around a longitudinal axis y.

A probe cover, when installed onto the probe, may be retained by one of many methods known in the art, some of which are described above. A preferred embodiment of a probe cover according to the present invention includes middle and distal portions which are not substantially different from those of above-described prior art. It should be noted that the present invention is principally directed to providing additional features in a proximal portion of a probe cover for precisely matching the probe cover to a corresponding thermometer.

Figure 3:
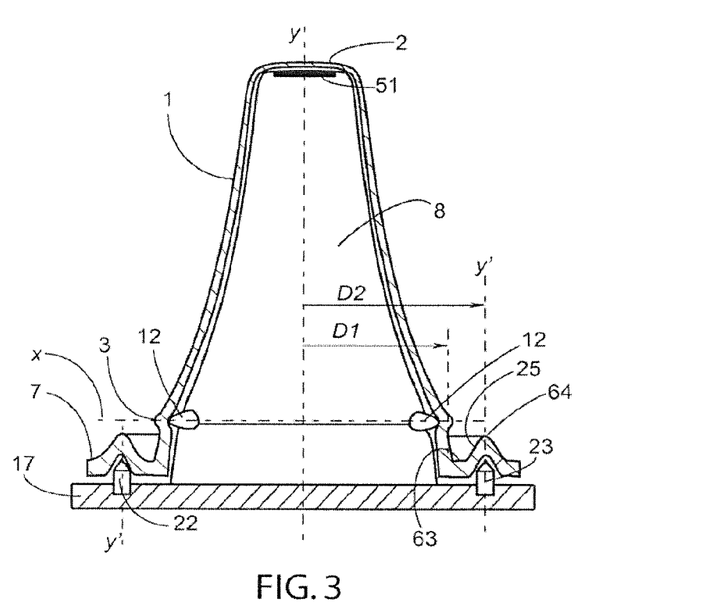
FIG. 3 provides a side cross-sectional view of a unitary probe cover according to an embodiment of the present invention.

The probe cover of FIG. 3 is a unitary IR probe cover having a membrane 2 adjacent to an IR window 51 of the IR thermometer's probe 8. Side wall 1 of the probe cover envelopes sides of the probe 8. A circular offset 3 of the probe cover snaps over nipples 12 of the probe 8, thus assuring retention of the probe cover when installed onto the probe 8. Preferably, two or more nipples 12 are opposingly provided on the sides of the probe 8. As shown in FIG. 3, nipples 12 and offset 3 are disposed along a transverse axis x that is normal to the longitudinal axis y.

In the proximal or base portion of the probe cover of FIG. 3, a brim 7 is provided and disposed in a direction substantially parallel to the transverse axis x. The brim 7 includes a pre-formed fold 25 that extends upwardly in a direction parallel to the longitudinal axis y. The fold 25 may be continuously formed around the longitudinal axis y, or may be broken into two or more segments. A front end 17 of the IR thermometer contains at least one pin 23 that enters the fold 25 as the probe cover is installed and seated on the probe. Preferably, two or more pins (23 and 22) are provided on the IR thermometer front end 17 for entering the fold 25. If the pins 22 and 23 and the fold 25 are not matched (for example, if the probe cover is not intended to be used with the IR thermometer), the mismatch (between the shapes and positions of fold 25 and pins 23 and 22) prevents the probe cover from sitting deeply enough on the probe 8 to be seated. As a result, the offset 3 is not able to engage with the nipples 12, and the probe cover is not effectively retained for use on the probe 8.

Figure 4A:
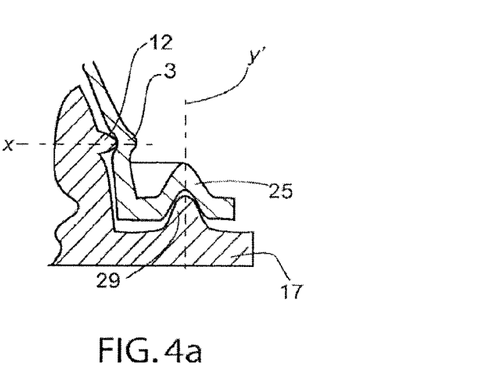
FIG. 4a is a partial view of a probe cover according to another embodiment of the present invention.

Alternatively to the pins 22 and 23, a matching ridge 29 may be formed as part of the IR thermometer front end 17 (see, e.g., FIG. 4a). For a secure seating of the probe cover on the probe 8 that causes the nipples 12 to be engaged with the probe cover offset 3, ridge 29 must have a complimentary shape to fold 25. The fold 25 and the corresponding pins 22 and 23, or the ridge 29 are substantially disposed along a matching axis y' that is substantially parallel to the longitudinal axis y and normal to the transverse axis x. Having a ridge 29 that is too wide or is centered at a wrong distance D2 from the longitudinal axis y for a particular probe cover, will prevent such probe cover from being retained on the probe.

A fold 25 is just one suitable example of a mechanical mating feature according to the present invention. Another example is a dip 61 (see, e.g., FIG. 4b) provided on the brim 7, with a complementary valley 62 provided on the thermometer front end 17. The dip 61 is essentially a half fold substantially formed along matching axis y' that is parallel to the longitudinal axis y and perpendicular to the transverse axis x. In the half fold arrangement, the brim 7 extends laterally outwardly from the matching axis y' rather than forming the second half of the fold as illustrated in the fold 25 of FIG. 4a.

Alternatively, a combination of a dip and a fold (or several of them) may be also employed in the probe cover and matched with the corresponding complementary features on the thermometer.

Figure 4B:
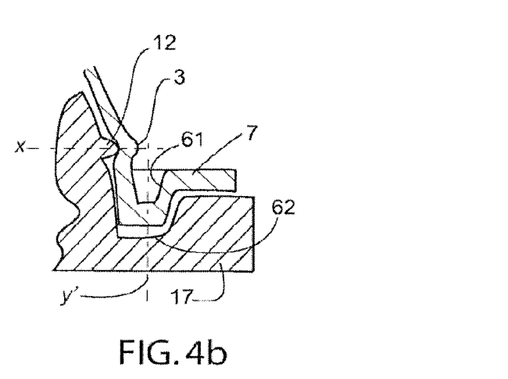
FIG. 4b is a partial view of a probe cover according to a further embodiment of the present invention.

In each of the above-described embodiments of the present invention, the mating features such as a fold 25 and dip 61 shown in FIGS. 3, 4a and 4b (formed along the matching axis y') and their corresponding mating features 22, 23 and 29 formed on the probe are positioned further from the longitudinal axis y than the retention features such as offset 3 and nipple 12 (see, e.g., respectively corresponding distances D2 and D1).

The mating features on the IR thermometer may further be aligned with a probe cover ejector. For example, after a temperature measurement is complete, the probe cover can be removed (ejected) from the probe by disengaging nipples 12 from offset 3 (see, e.g., FIG. 5b). A disengagement can be accomplished by a simple manual pulling off of the probe cover. Alternatively, the disengagement may be assisted by an ejector that is part of the thermometer.

Figure 5A:
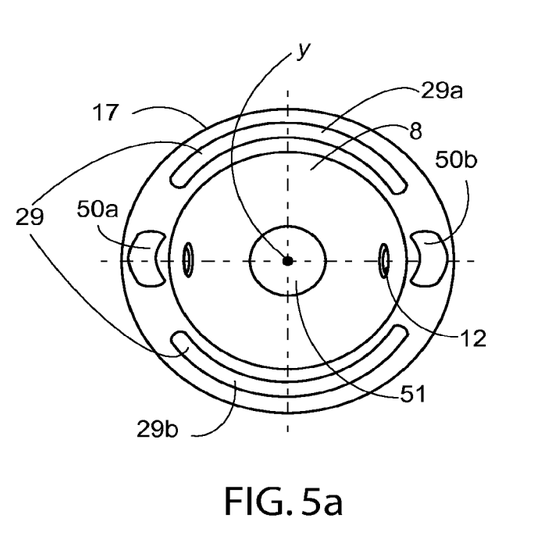
FIG. 5a shows a front elevational view of a probe cover according to another embodiment of the present invention.

FIG. 5a depicts a front elevational view of the front end 17 of the thermometer as viewed along longitudinal axis y. No probe cover is installed. FIG. 5a illustrates a ridge 29 broken into two segments 29a and 29b. In between these segments, two ejectors 50a and 50b are positioned. The ejectors are normally hidden below the surface of the front end 17, and have shapes and/or locations that are not matching the shape (for example, being wider than) and/or location of the ridge 29.

Ejection of a probe cover is facilitated, for example, by moving ejectors 50a and 50b upwardly in along axis y'. Because the ejectors 50a, 50b do not match the shapes of the segments 29a, 29b, the ejectors 50a, 50b when operated will not fully enter the fold 25 of the probe cover, and will act therefore to push the probe cover upwardly in a direction parallel to the axis y. The IR thermometer may include one or more ejectors. Each ejector is preferably positioned adjacent to one of the nipples 12 of the IR thermometer.

Figure 5B:
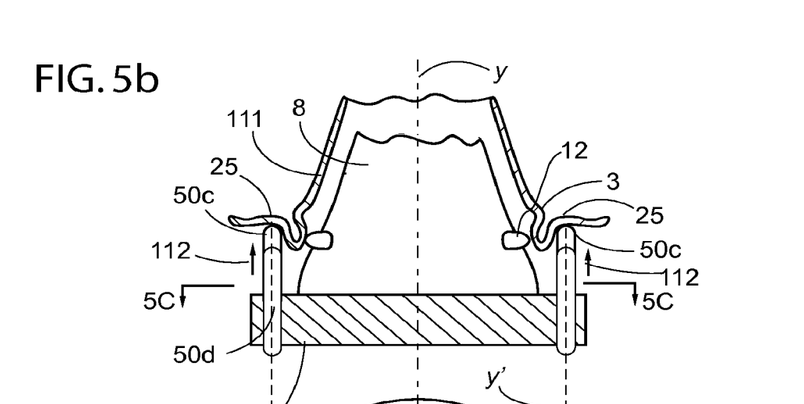
FIGS. 5b and 5c respectively show a side cross-sectional view of a probe and probe cover according to a further embodiment of the present invention and a front elevational view of the probe.
Figure 5C:
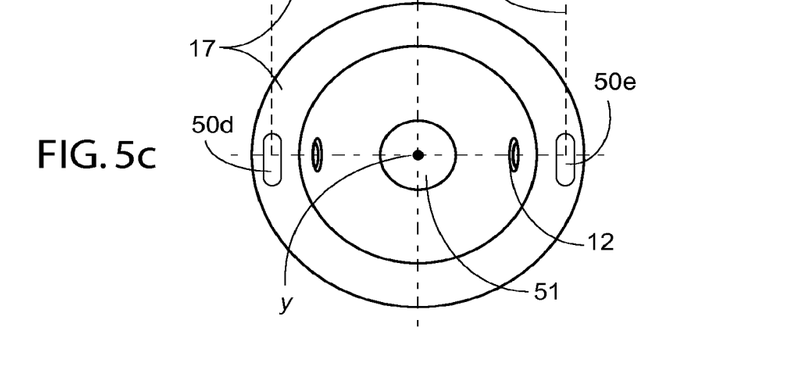

Alternatively, the ejectors may be configured to serve a dual purpose: providing a matching feature for retaining the probe cover, as well as an ejecting feature. For example, as illustrated in FIG. 5b, when ejectors 50d and 50e are partially retracted (that is, when only portions 50c extend above an upper surface of the front end 17), the ejectors 50d and 50e may serve as ridges for mating with the probe cover fold 25 as illustrated in FIG. 3. When partially retracted, the portions 50c provide just enough height to match with the fold 25, and allowing the probe cover 111 to slide sufficiently downward for engaging the offset 3 and nipples 12. However, when fully extended in a direction 112 as shown in FIG. 5b, the ejectors 50d, 50e will push the probe cover 111 outwardly and disengage offset 3 from nipple 12. Preferably at least two ejectors 50d, 50e are positioned near two respective nipples, making two nipple-ejector pairs. Each pair is preferably disposed in opposition along the sides of the probe 8. Each ejector is disposed along the axis y' that is parallel to the longitudinal axis y. FIG. 5c illustrates a front elevational view of the probe 8 which further shows the positioning of the ejectors 50d, 50e.

Figure 6:
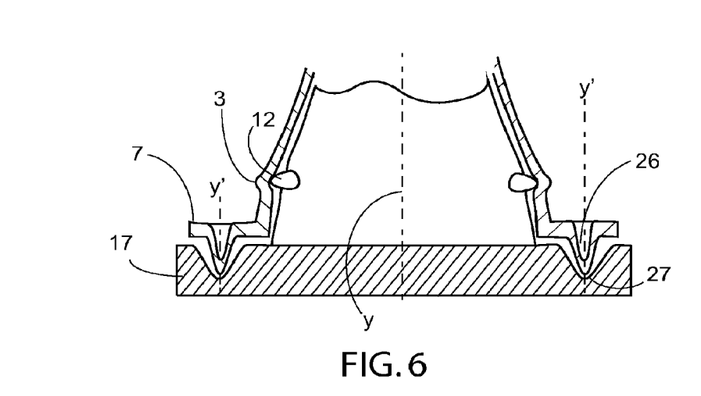
FIG. 6 shows a partial cross-sectional view of a probe cover according to another embodiment of the present invention.

FIG. 6 illustrates probe cover according to the present invention which includes an outward fold 26 on the brim 7 for mating with valley 27 formed in the front end 17 of the thermometer. The fold 26 on the brim 7 extends downwardly along the axis y' that is parallel to the longitudinal axis y.

Figure 7:
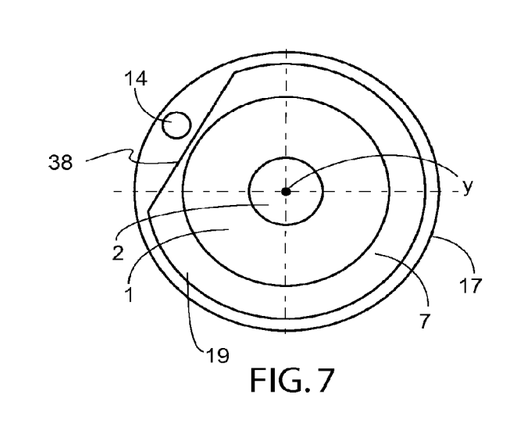
FIG. 7 shows a front elevational view of a probe cover according to another embodiment of the present invention.
Figure 8:
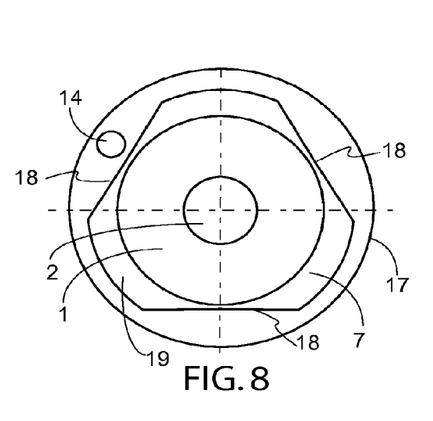
FIG. 8 shows a front elevational view of a probe cover according to a further embodiment of the present invention.

Numerous other shapes and mechanical mating arrangements can be formed on the proximal portion of the probe cover and the corresponding front end 17 or probe 8 of a thermometer. For example, as shown in FIGS. 7 and 8, a circular brim 19 may be trimmed or relieved with a cut 38 forming a chord or linear segment between two points on the perimeter of the circular brim 19, to facilitate matching or clearance in relation to a pin 14 projecting from the thermometer front end 17. Any number of additional cuts may be added as needed for a particular design. For example, FIG. 8 show a probe cover having three cuts 18 made equidistantly around the brim 19. The cuts 38 and 18 are made to match the positions of one or more pins 14, or other complementary features disposed on the thermometer front end 17

Figure 9:
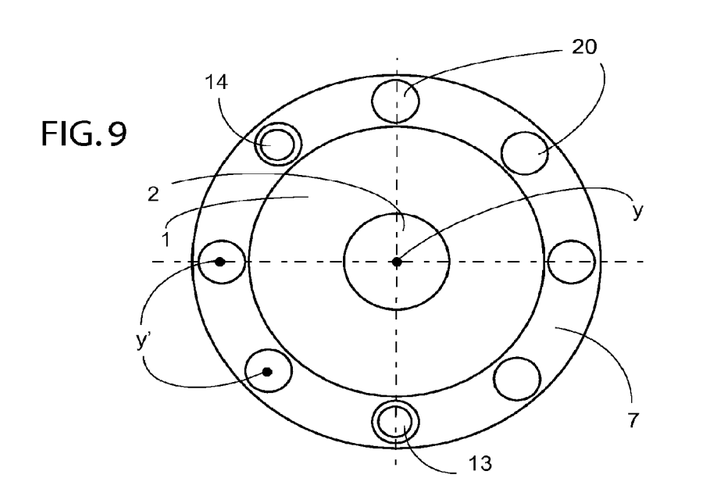
FIG. 9 shows a front elevational view of a probe cover according to another embodiment of the present invention.
Figure 10A:
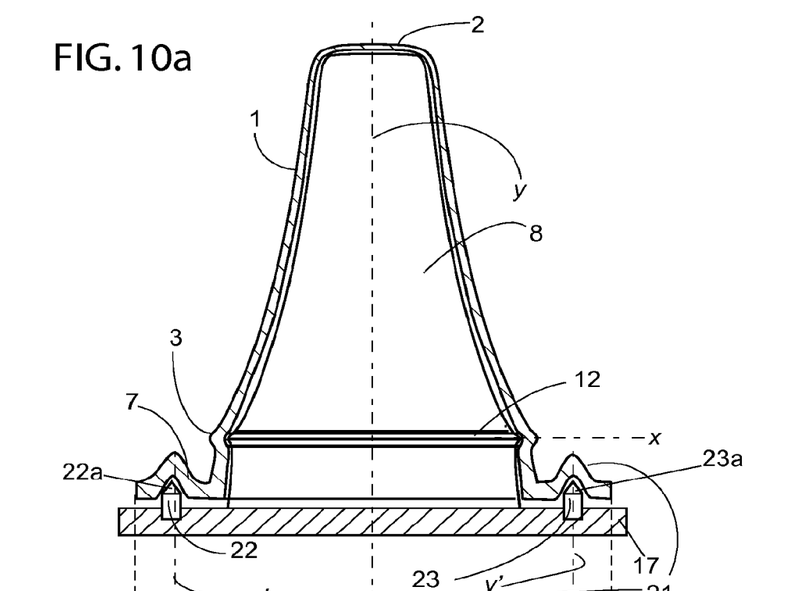
FIGS. 10a and 10b respectively show a side cross-sectional view and a front elevational view of a probe cover according to a further embodiment of the present invention.
Figure 10B:
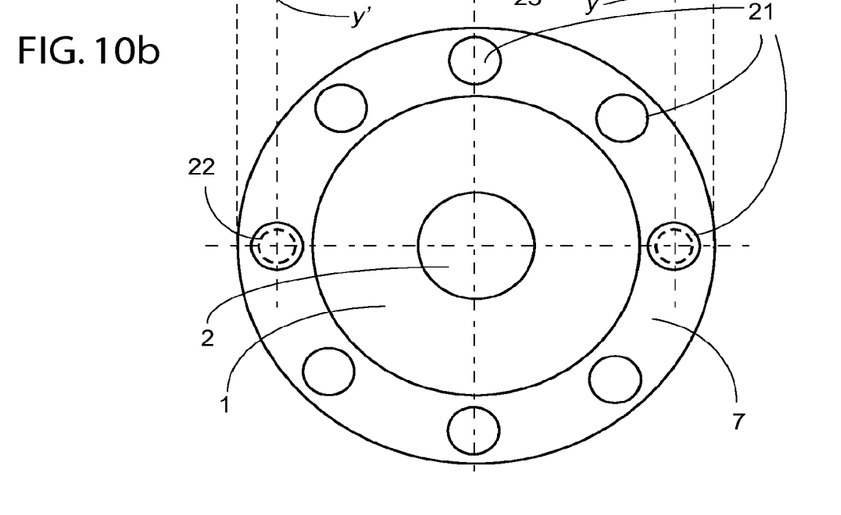

Another embodiment of the present invention is shown in FIG. 9. In this embodiment, one or more holes 20 are formed in the brim 7 of the probe cover along matching axes y' that are parallel with the longitudinal axis y. In an embodiment having at least two holes 20, mating pins 13 and 14 are positioned on the front end 17 to match the sizes and locations of holes 20. For example, the lateral distance of the pins 13 and 14 from the longitudinal axis y and the angular relationship between the pins 13 and 14 with reference to the longitudinal axis y is matched by the positioning of the holes 20 in the brim 7 of the probe cover when the probe cover is seated on the probe As an alternative to the holes 20, conical or similarly-shaped extensions 21 can be formed on brim 7 as depicted in FIGS. 10a and 10b. For a unitary probe cover, they may be preferably formed by use of a thermoforming technology. In this case, mating pins 22, 23 formed on the front end 17 include conical or similarly-shaped features 22a, 23a for effectively mating with the conical or similarly-shaped extensions 21.

Figure 11A:
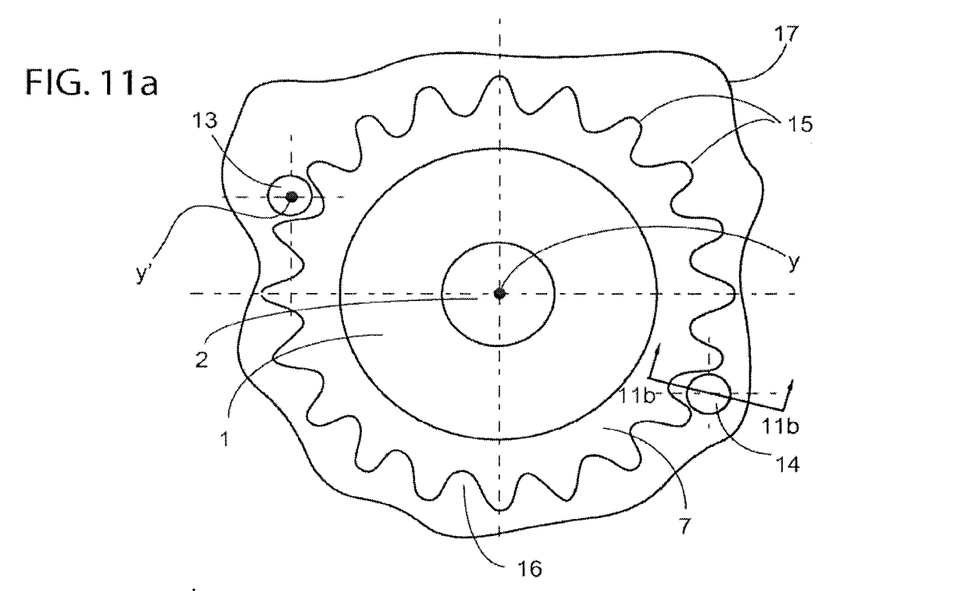
FIG. 11a shows a front elevational view of a probe cover according to another embodiment of the present invention.

Another embodiment of the present invention having yet another mechanical mating feature is shown in FIG. 11a. In FIG. 11a, the brim 7 has petals 15 formed by indentations (voids) 16 spaced around a circumference of the brim 7. One or more mating pins (for example, the pins 13 and 14) on the thermometer front end 17 allows for the probe cover installation along longitudinal axis y. In this embodiment of the invention, the pins 13 and 14 are positioned to simultaneously enter the voids 16 between the petals to form a "key-lock" arrangement. The locking arrangement is shown in more detail in FIG. 11b.

Figures 11B, 12:
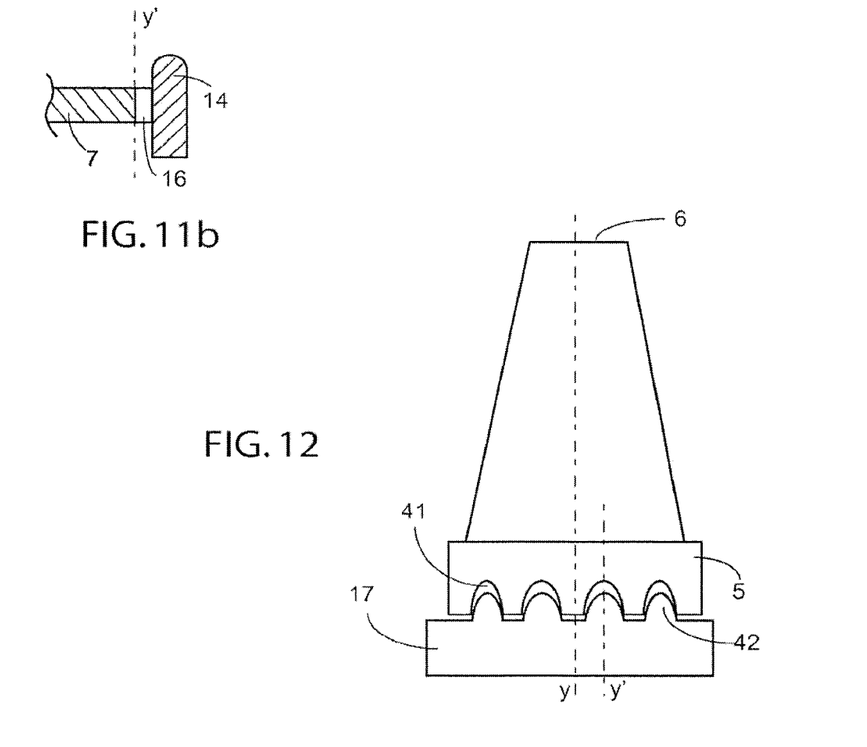

In another embodiment of the present invention illustrated in FIG. 12, a two-piece probe cover 55 has a matching feature formed as semi-oval cut-outs 41 in the bottom ring 5 that match corresponding semi-oval fingers 42 of the front end 17 when the probe cover is installed and seated. Any number of other complementary shapes may alternatively be used for the cut-outs and corresponding fingers. The cut-outs 41 are provided along the axes y' that are parallel to the longitudinal axis y.

The above described matching features all are of a mechanical nature. In another embodiment of the present invention, a non-mechanical matching feature between the probe and probe covers is provided using opto-electronic devices. As shown for example in FIG. 13, a brim 7 of the probe cover is provided with a reflective layer 30 formed on an underside surface of the brim 7 facing a thermometer body 31. The layer 30 may include, for example, an aluminum foil that is welded, glued, sputtered or otherwise deposited on the underside surface brim 7. Alternatively, the reflective layer 30 may be a painted layer of selected color.

Figure 13:
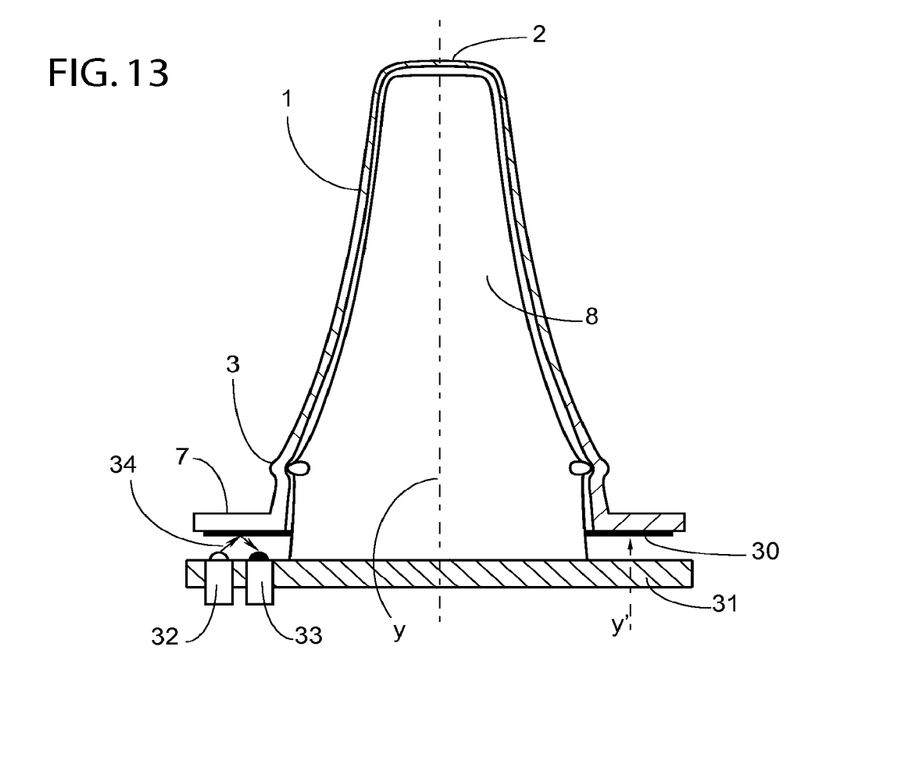
FIG. 13 shows a side cross-sectional view of a probe cover according to another embodiment of the present invention.

As illustrated in FIG. 13, the thermometer body 31 carries a light emitter 32 and light detector 33 that together form an opto-coupler. When a probe cover with the reflective layer 30 is installed, the detector 33 is configured to receive a light beam 34 that is transmitted by the light emitter 32 and reflected by the layer 30. Detector 33 will respond with a changing electrical signal, thus signaling a detection circuit in the IR thermometer that a suitable probe cover has been properly installed. If the detector 33 detects no reflection, or detects a reflection having a wrong intensity or mismatched spectral characteristics (color), the detection circuit preferably determines that a suitable probe cover has not been installed, and will prevent a temperature measurement from being initiated in the IR thermometer.

If the reflective layer 30 has been painted with a particular color, the color of the emitter 32 should be substantially the same to allow for proper reflection of the emitted light. For example, if emitter 32 generates green light and the reflector 30 is also green, then there will be reflection of the emitted light which will then be detected by detector 33. However, if emitter 32 generates green light and the selected color of the reflector 30 is red, there will be a negligible reflection of green light toward detector 33 and the device will indicate a mismatch, i.e., a proper probe cover has not been used. A spectral response of detector 33 should be matched with the spectral response of the emitter 32.

Figure 14:
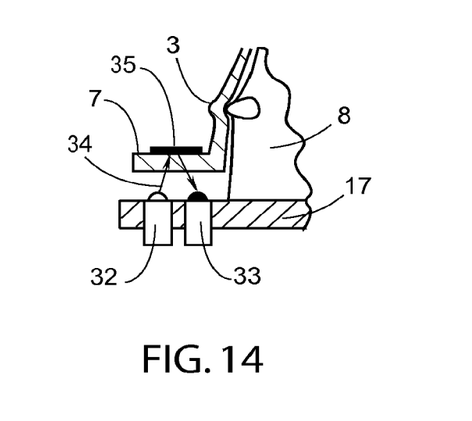
FIG. 14 shows a partial cross-sectional view of a probe cover according to a further embodiment of the present invention.

Alternatively, as shown in FIG. 14, the reflective layer 35 may be deposited on a side of brim 7 opposite to the underside. In this embodiment of the invention, the light beam 34 will travel through brim 7 on the way to detector 33. This will not change the operation of the opto-coupler 32, 33 and detection circuit, provided that the brim 7 of the probe cover is suitably transparent.

Figure 15:
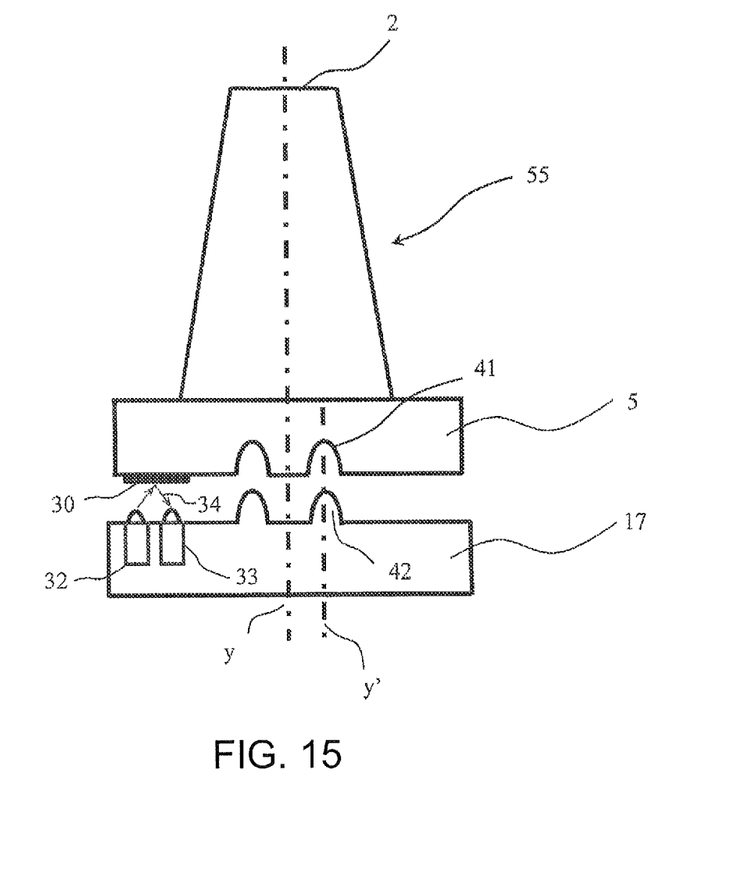
FIG. 15 shows a side cross-sectional view of a probe cover according to another embodiment of the present invention.

In another embodiment of the present invention illustrated in FIG. 15, a probe cover 55 has a matching feature formed as cut-outs or recesses 41 in the bottom ring 5 that match corresponding figure or projections 42 of the front end 17 of the thermometer when the probe cover is installed and seated. Any number of other complementary shapes may alternatively be used for the cut-outs and corresponding fingers. The cut-outs 41 are provided along the axes y' that are parallel to the longitudinal axis y. FIG. 15 also shows that the underside of the probe cover 55 is provided with a reflective layer 30. The thermometer body front end 17 carries a light emitter 32 and light detector 33 that together form an opto-coupler. When a probe cover with the reflective layer 30 is installed, the detector 33 is configured to receive a light beam 34 that is transmitted by the light emitter 32 and reflected by the layer 30.

While the invention has been particularly shown and described with reference to preferred embodiments thereof, it will be understood by those skilled in the art as described herein that various changes in form and details may be made to the discloses embodiments without departing from the spirit and scope of the invention. For example, in relation to the embodiments having mechanical matching features, the embodiment of FIG. 10 could be modified to provide pin features in the brim of the probe cover while providing conical or similarly-shaped extensions in the surface of the front end of the thermometer. In addition, in relation to the embodiments having non-mechanical matching features, the reflector and optical circuits could respectively be replaced with an electrical component (for example, a film resistor) and circuits for measuring a selected characteristic of the electrical component (for example, a selected resistance).

Accordingly, the invention is to be limited only by the scope of the claims and their equivalents.

What is claimed is:

1. A probe cover for covering a probe that extends from a housing of a thermometer, the housing of the thermometer having one or more projections, the probe cover comprising:

a tip portion configured for covering a distal end of the probe;
a base portion configured for retaining the cover at a proximal end of the probe, the base portion including a brim with one or more matching features, the matching features comprising a reflective layer disposed around the brim; and
a body portion disposed between the tip portion and the base portion,
wherein:
the tip portion, the body portion and the base portion are sequentially disposed in a direction along a longitudinal axis of the probe cover; and
the base portion further includes one or more recesses extending in a direction parallel to the longitudinal axis and corresponding to the one or more projections, which are disposed on the housing of the thermometer.

2. The probe cover of claim 1, wherein the reflective layer comprises a metal foil.

3. A thermometer, comprising:
a housing;
a probe extending from the housing along a longitudinal axis, the probe being configured for receiving thermal energy indicative of a temperature; and
a probe cover for covering the probe,
the probe cover comprising:
a tip portion configured for covering a distal end of the probe;
a base portion configured for retaining the probe cover at a proximal end of the probe; and
a body portion disposed between the tip portion and the base portion, wherein the tip portion, the body portion and the base portion are sequentially disposed in a direction along the longitudinal axis,
wherein:
the base portion further includes:
at least one protrusion extending laterally away from the longitudinal axis for engaging a locating element of the probe to locate the cover at a seating position along the longitudinal direction, and
a brim, the brim including a reflective layer;
the thermometer further comprises:
a light emitter and a light detector, the light emitter is operative to emit light energy toward the reflective layer and the light detector is operable to detect light energy reflected by the reflective layer, and wherein the emitted light energy and the reflected light energy are transmitted in a substantially unobstructed manner between the reflective layer and one or more of the light emitter and the light detector; and
matching features, the matching features comprising one or more recesses in the base portion of the probe cover, the one or more recesses extending in a direction parallel to the longitudinal axis, and one or more projections disposed on the housing, the one or more projections corresponding to the one or more recesses and extending in a direction parallel to the longitudinal axis.

4. The thermometer of claim 3, wherein:
the thermometer further comprises a detection circuit for determining whether the detected light energy meets a predetermined criteria.

* * * * *